United States Patent
Wallach (10) Patent No.: US 6,755,026 B2
(45) Date of Patent: Jun. 29, 2004

(54) THERMOELECTRIC SYSTEM TO DIRECTLY REGULATE THE TEMPERATURE OF INTRAVENOUS SOLUTIONS AND BODILY FLUIDS

(75) Inventor: John M. Wallach, Diamond Bar, CA (US)

(73) Assignee: Tech Medical Devices Inc., Diamond, CA (US)

( * ) Notice: Subject to any disclaimer, the term of this patent is extended or adjusted under 35 U.S.C. 154(b) by 0 days.

(21) Appl. No.: 10/279,100

(22) Filed: Oct. 24, 2002

(65) Prior Publication Data

US 2004/0079089 A1 Apr. 29, 2004

(51) Int. Cl.[7] .............................. F25B 21/02; A61F 7/00
(52) U.S. Cl. ............................. 62/3.7; 62/3.3; 607/106
(58) Field of Search ........................... 62/3.2, 3.3, 3.7; 607/105, 106

(56) References Cited

U.S. PATENT DOCUMENTS

| | | | | |
|---|---|---|---|---|
| 2,928,253 A | * | 3/1960 | Lopp et al. .................... | 62/3.3 |
| 2,931,188 A | * | 4/1960 | Levit ............................ | 62/3.3 |
| 3,191,391 A | * | 6/1965 | Muller .......................... | 62/3.3 |
| 3,206,937 A | | 9/1965 | Walisch et al. | |
| 3,293,868 A | | 12/1966 | Gonzalez | |
| 3,399,536 A | * | 9/1968 | Walz ............................ | 62/3.2 |
| 3,475,590 A | | 10/1969 | Pins | |
| 4,309,592 A | | 1/1982 | Le Boeuf | |
| 4,476,685 A | * | 10/1984 | Aid .............................. | 62/3.3 |
| 4,574,876 A | * | 3/1986 | Aid ............................. | 165/46 |
| 5,349,821 A | * | 9/1994 | Schrage ......................... | 62/3.7 |
| 5,561,981 A | * | 10/1996 | Quisenberry et al. ......... | 62/3.7 |
| 5,564,276 A | * | 10/1996 | Abadilla et al. .............. | 62/3.7 |
| 5,899,077 A | | 5/1999 | Wright et al. | |
| 5,966,940 A | | 10/1999 | Gower et al. | |
| 6,003,319 A | * | 12/1999 | Gilley et al. .................. | 62/3.7 |
| 6,045,752 A | * | 4/2000 | Elgas ........................... | 422/46 |
| 6,230,497 B1 | * | 5/2001 | Morris et al. ................. | 62/3.7 |
| 6,233,944 B1 | * | 5/2001 | Yamada et al. ............... | 62/3.7 |

FOREIGN PATENT DOCUMENTS

FR 2702830 9/1994

* cited by examiner

Primary Examiner—William C. Doerrler
(74) Attorney, Agent, or Firm—Birch, Stewart, Kolasch & Birch, LLP (57) ABSTRACT

A system, method and apparatus for temperature regulation of physiological fluids is disclosed. In an exemplary system for use in cardiopulmonary procedures, blood is entered into a proportionally long, narrow disposable container, is heated or cooled to a desired temperature, and exits from an opposite end. The disposable container includes a pair of long, flat surfaces facing each other in relatively, close proximity. The blood is transitioned from transport tubing into a thin laminar flow layer and back into tubing, inside the container. This container is placed in a heat exchange device having thermoelectric modules that contact the majority of surface area, opposite the blood side in the container. The thermoelectric modules act as fully reversible heat pumps and move heat from one side of the module to the other, dependant on the direction of the current supplied to the modules. Feedback from sensors in the fluid path independently control each thermoelectric module.

19 Claims, 7 Drawing Sheets

THERMOELECTRIC SYSTEM TO DIRECTLY REGULATE THE TEMPERATURE OF INTRAVENOUS SOLUTIONS AND BODILY FLUIDS

BACKGROUND OF THE INVENTION

1. Field of the Invention

The present invention relates to an apparatus and method for heating and/or cooling sterilized fluids. In particular, the present invention relates to a method and device for heating and cooling physiological fluids such as blood, that may be administered to a patient during medical procedures.

2. Description of the Background Art

The invention relates to a device for heating sterilized fluids, such as blood or other fluids that are to be administered to a patient. It is frequently necessary during the course of medical treatment to heat or cool physiological fluids. For example, haemodialysis removes waste products from the blood by passing it out of the body, through a filtering system (dialyser) and returning it, cleaned, to the body. While in the filtering system, the blood flows through tubes made of a membrane that allows the waste products (which are much smaller than blood cells) to pass out through it. It is common practice to heat the dialysis fluid before it enters the blood dialyzer to aid in filtering.

In the collection of whole blood from donors, it is sometimes desirable to cool the collected blood prior to further processing. Plasmapheresis, or plasma exchange, is a procedure in which blood is separated into cells and plasma. The plasma is removed and replaced with fresh frozen plasma and/or a plasma substitute. Similarly, in plasmapheresis, when blood is taken from a donor and separated, it is desirable to have heating apparatus or cooling apparatus available prior to further handling of the separated fractions.

If a component fraction were to be returned to the patient, it would be advantageous to warm this fraction to approximately body temperature prior to such return. On the other hand, apparatus for cooling may be needed if the separated plasma fraction is to be subjected to further processing.

Alternatively, heating may be used in connection with the transfusion of blood that has been refrigerated and needs to be warmed before the patient is transfused.

In other circumstances, it may be necessary or desirable to effect heating or cooling on a continuous basis. In blood dialysis, for example, it is customary to heat the dialysate prior to passing it through the dialyzer. In plasmapheresis procedures, it may be desirable to cool either the separated cellular fraction or the separated plasma fraction on a continuous basis.

Medical research has demonstrated that rapid cooling of a patient's body temperature following a cerebral stroke or other serious trauma significantly improves the prognosis. Several devices employing alternate technologies are currently being clinically evaluated. Companies such as "Innercool" and "Alicius" have been promoting catheter based cooling driven by the use of refrigeration.

In Cardiopulmonary Bypass (CPB) surgery, the body temperature of the patient is dropped below normal temperature during surgery and then returned to normal temperature towards the end of the procedure. This is accomplished by regulating the temperature of the extra-corporeal blood by means of a heat exchanger integrated with an oxygenator.

However, the task of heating or cooling of the blood in the CPB circuit is difficult for a variety of reasons. Perfusionists use typically complex heat exchangers, with large surface area, to circulate water opposite the blood in order to regulate the temperature of blood. It is critical to maintain the temperature differential between the water and blood within 10 degrees.

During CPB surgery, cardioplegia is administered at very low temperatures. This is accomplished by using water-based heat exchangers. The inadequacies of current devices has necessitated the use of ice to assist in the cooling process. This has minimized the ability for temperature regulation, but it is still a common practice.

Typical CPB heat exchanger configurations are inconvenient to use and present many problems to practitioners. It is often difficult to adhere to the surgeon's temperature protocol. An undetected water to blood leak can lead to hemolysis which can be catastrophic to the patient's well being. Further, the risk of complications due to exposure to foreign surfaces is well documented. Companies such as Cardioventions have been striving to capitalize on the advantages of reduced blood contact surface area.

U.S. Pat. No. 4,309,592 to Le Boeuf and U.S. Pat. No. 4,476,685 to Aid describe apparatus for heating or cooling physiological fluids utilizing thermoelectric/resistive heating elements arranged in a spaced apart relationship. A flexible container is disposed within a space formed between the two heating elements. Heat sinks or fins are also provided in order to effectuate heat transfer.

U.S. Pat. No. 5,899,077 to Wright et al. describes an apparatus for the heating and cooling of high purity and/or corrosive fluids. Plastic tubing containing the fluid is interposed and press-fitted between a pair of heat exchanger plates that further sandwich a thermoelectric module. A thermally conductive grease is further provided to enhance contact between the plastic tubing and a base plate of one of the heat exchanger plates.

Similarly, U.S. Pat. No. 3,293,868 to Gonzalez describes a cooling apparatus having a base with a collector plate mounted therein. A flexible tube carrying a fluid is routed and coiled between guide fins toward the center of the collector plate. A thermocouple engaged with a transfer block is included with a heat-dissipating assembly.

The devices and methods of the background art suffer from the following disadvantages. For the medical procedures and devices described hereinabove, water has been the preferred energy transfer medium to effect the desired temperature change. However, the use of water presents patient safety issues that are well documented. In some cases, electrical resistance has been used as an alternative. While this eliminates water, desired performance has been difficult to achieve and cooling is not possible or is otherwise inefficient.

If performance standards can be met, safety and convenience for medical procedures requiring temperature regulation would be improved by the elimination of water. This is especially true for the CPB circuit. A unique energy transfer system is required that meets the special energy transfer needs of medical procedures, i.e. the CPB circuit, and does not rely on water. The method and apparatus for temperature regulation in medical, especially cardiopulmonary, applications is embodied in the method and apparatus described hereinafter.

SUMMARY OF THE INVENTION

The present invention overcomes the shortcomings associated with conventional devices and methods, and achieves other advantages not realized by the background art.

It is an aspect of the present invention to provide a method and apparatus that eliminates the risk of blood hemolysis associated with water to blood leaks, including those that are often non-detectable. In addition to the safety risks to patients, procedures utilizing ice and water-based systems and methods require additional floor space, manpower and costs.

It is an aspect of the present invention to minimize the amount of foreign surface area required of a heat exchange device to thereby reduce the probability of systemic inflammatory response in patients.

It is an aspect of the present invention to minimize pumping volumes in order to reduce hemodilution of patients.

It is a further aspect of the present invention to improve heat exchange efficiency and to facilitate precise temperature control of heating and cooling protocols. A method, system and apparatus offering more efficient heat transfer and precise temperature control will lead to the reduction of the length of medical procedures, will free up valuable personnel resources such as surgeons and perfusionists, and will permit less-invasive medical procedures.

The present invention is a recognition, in part, that the ability provide safer methodologies that are intended to reduce the probability of post operative liabilities and complications, will promote quicker recoveries that result in shorter surgeries and patient stays.

These and other aspects of the present invention are accomplished by a heat exchange device for heating and cooling of a physiological fluid, the device comprising a pair of thermoelectric modules arranged in a spaced apart relationship; a container providing a flow path for the fluid, the container interposed between the thermoelectric modules; at least one heat sink for dissipating heat from the device; and at least one sensor arranged within the container and providing a temperature of the fluid along the flow path..

These and other aspects of the present invention are further accomplished by a system for controlling a fluid temperature of a physiological fluid, the system comprising a control system for setting and controlling the fluid temperature; a software program resident in the control system; a disposable container providing a flow path for the fluid; a plurality of thermoelectric devices arranged along and across the flow path of the container, wherein the container is interposed between the thermoelectric devices, the thermoelectric devices imparting individualized temperature control of the fluid temperature; a plurality of sensors arranged within the container and providing a temperature signal of the fluid to the control system; at least one heat pipe; and at least one heat sink for dissipating heat from the system.

These and other aspects of the present invention are further accomplished by a method for controlling a fluid temperature of a physiological fluid, the method comprising the steps of providing a disposable container having a flow path for the physiological fluid between a plurality of thermoelectric devices operatively connected to a control system; setting the fluid temperature of the fluid to a target temperature through the control system; and adjusting the fluid temperature with the thermoelectric devices to obtain the target temperature based upon temperature output signals received from a plurality of sensors arranged along and across the flow path.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

DETAILED DESCRIPTION OF THE PREFERRED EMBODIMENTS

Figure 1:
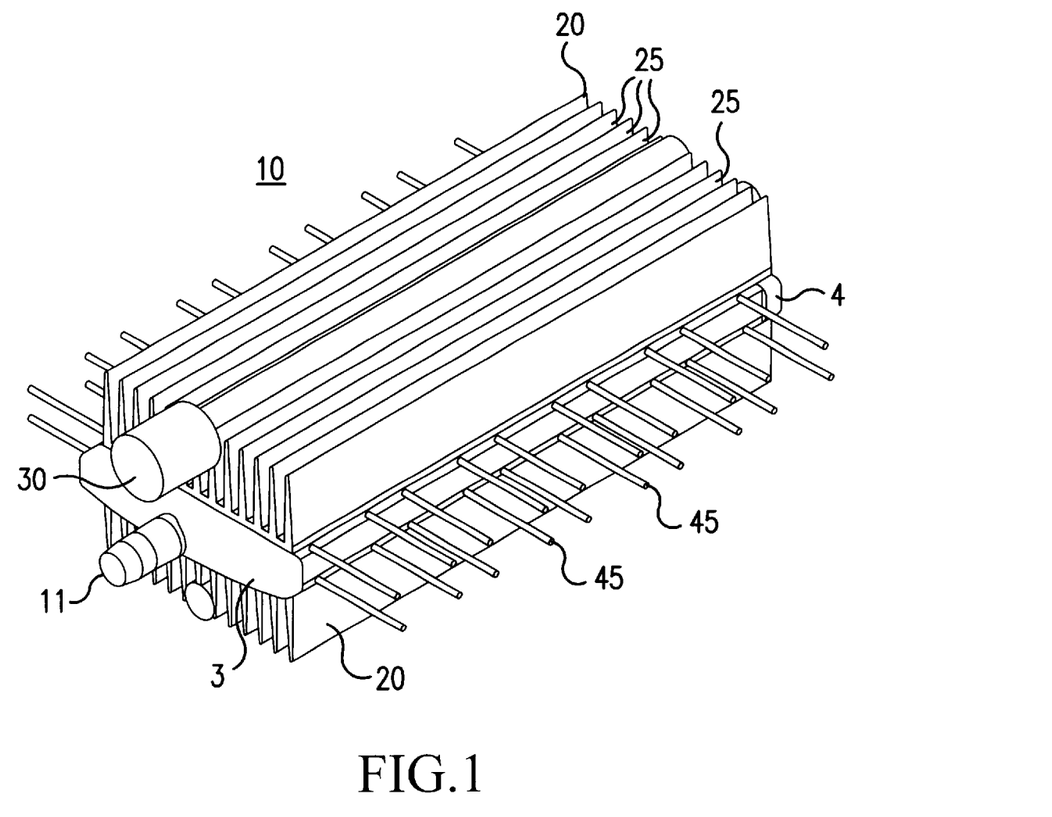
FIG. 1 is a perspective view of a heat exchange device according to an embodiment of the present invention.
Figure 2:
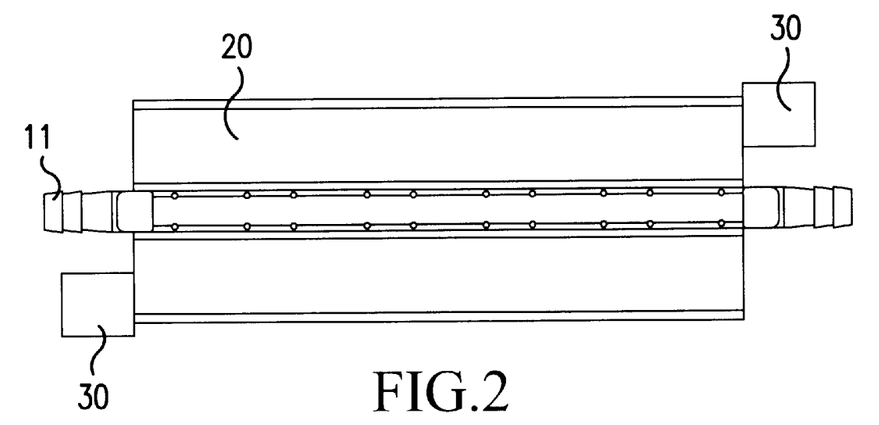
FIG. 2 is a side view of a heat exchange device according to an embodiment of the present invention FIG. 1.
Figure 3:
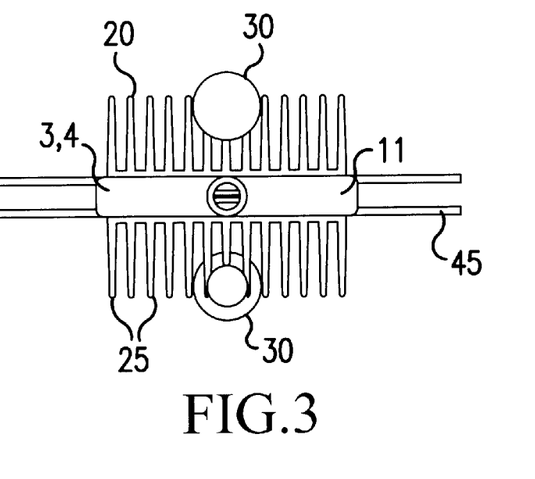
FIG. 3 is an end view of a heat exchange device according to an embodiment of the present invention.
Figure 4:
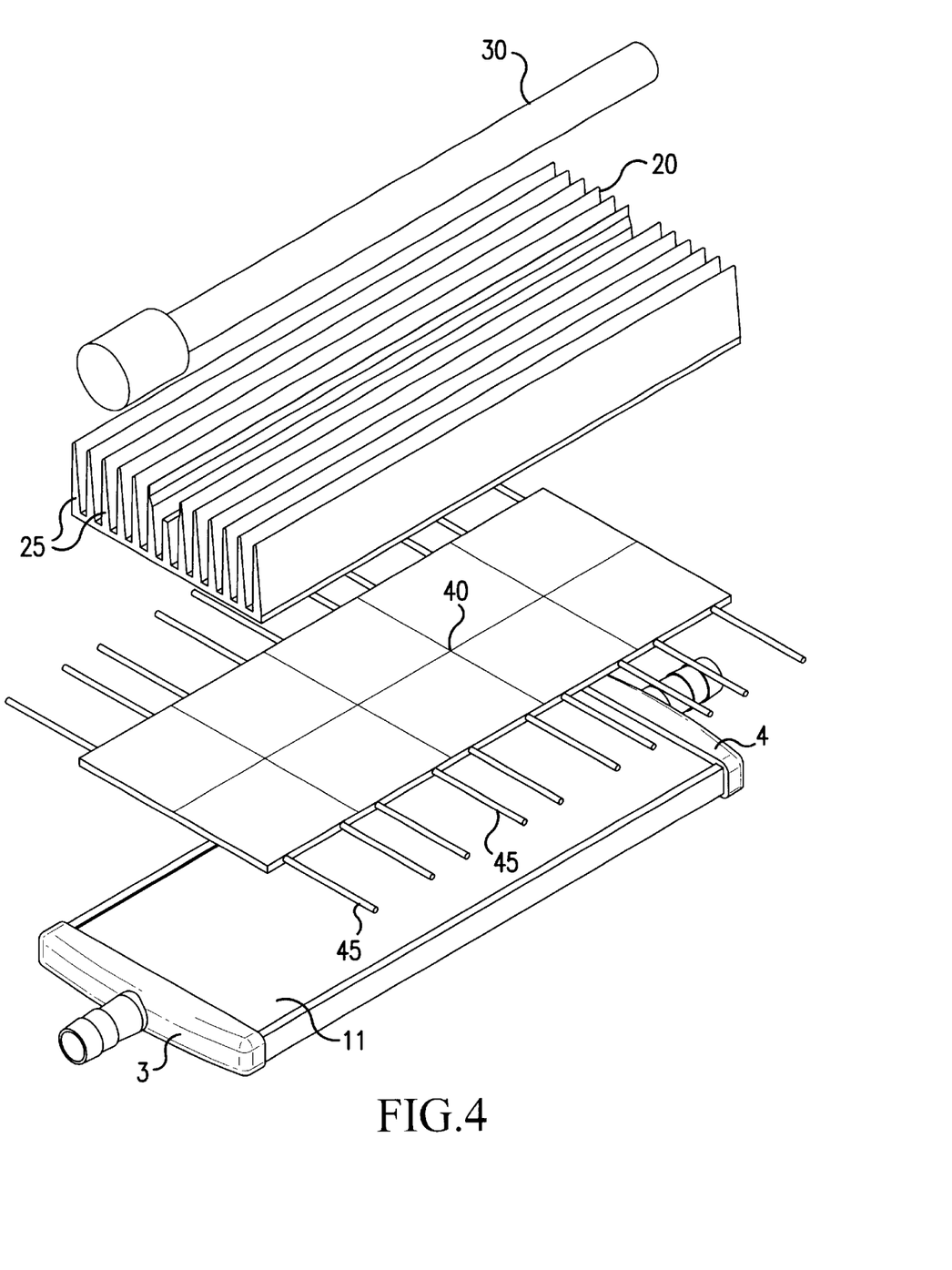
FIG. 4 is a partial, exploded perspective view of an upper half of a heat exchange device according to an embodiment of the present invention.
Figure 5:
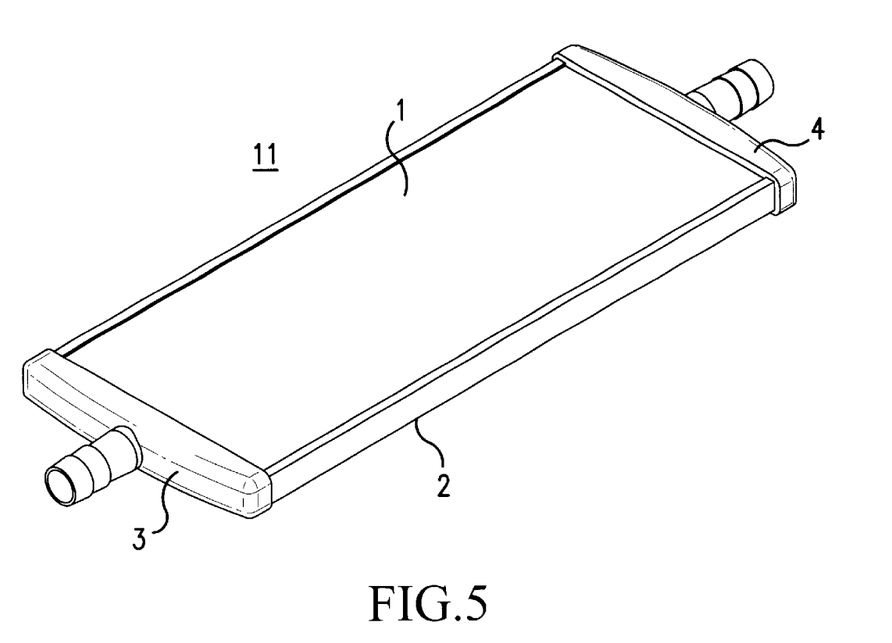
FIG. 5 is a perspective view of a disposable container according to an embodiment of the present invention.
Figure 6:
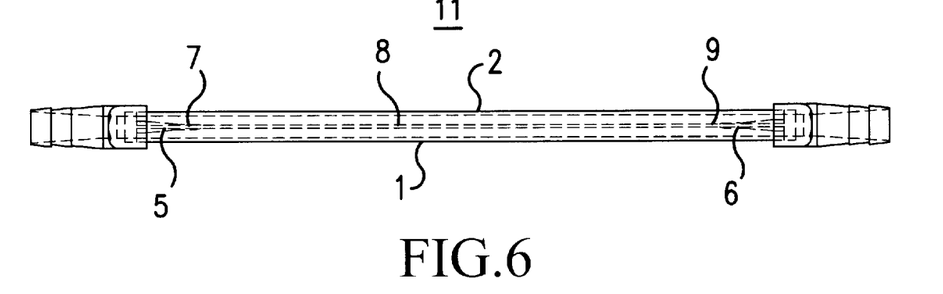
FIG. 6 is a side view of the disposable container shown in FIG. 5.
Figure 7:
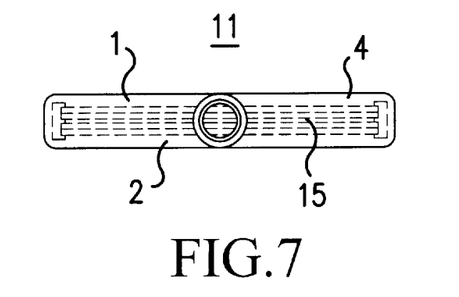
FIG. 7 is an end view of the disposable container shown in FIG. 5.
Figure 8:
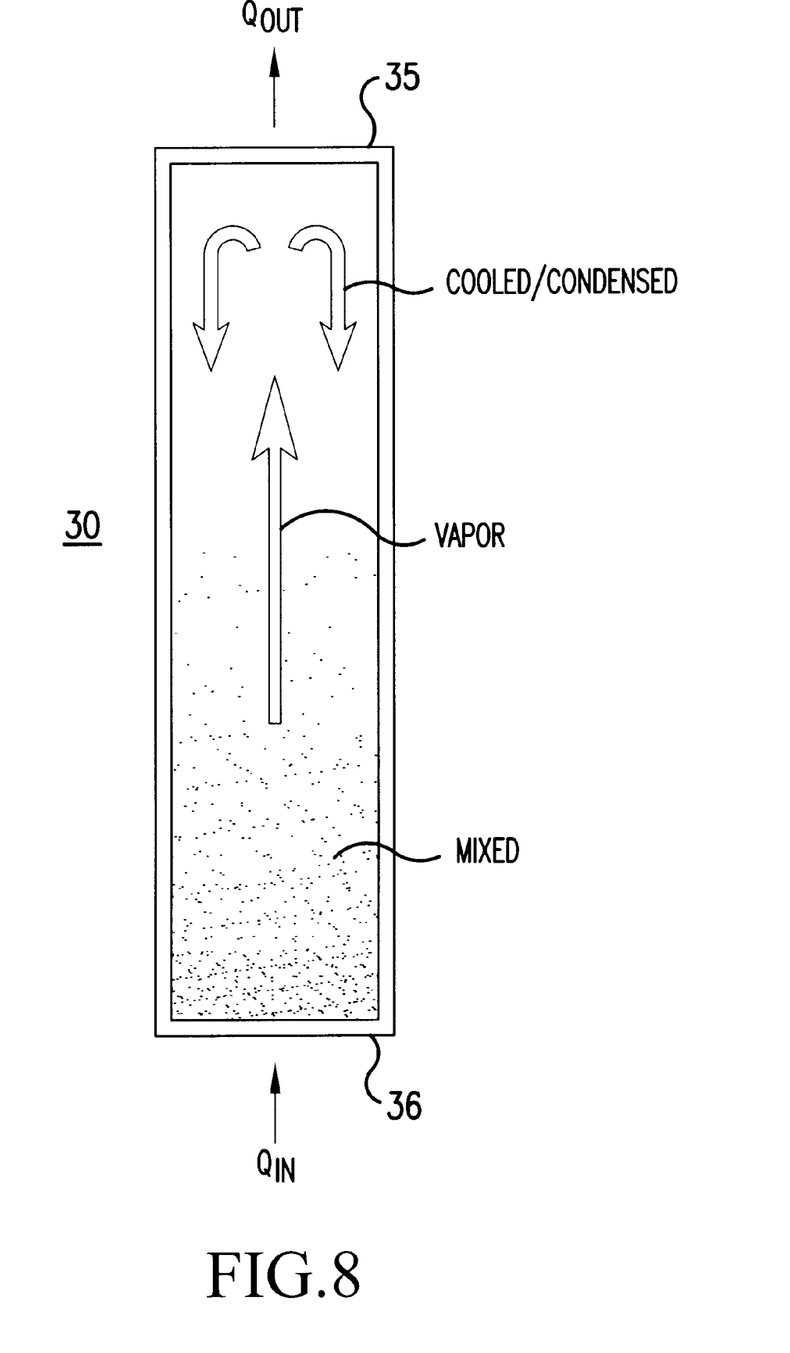
FIG. 8 is a side; cross-sectional, operational view of a heat pipe according to an embodiment of the present invention.
Figure 9:
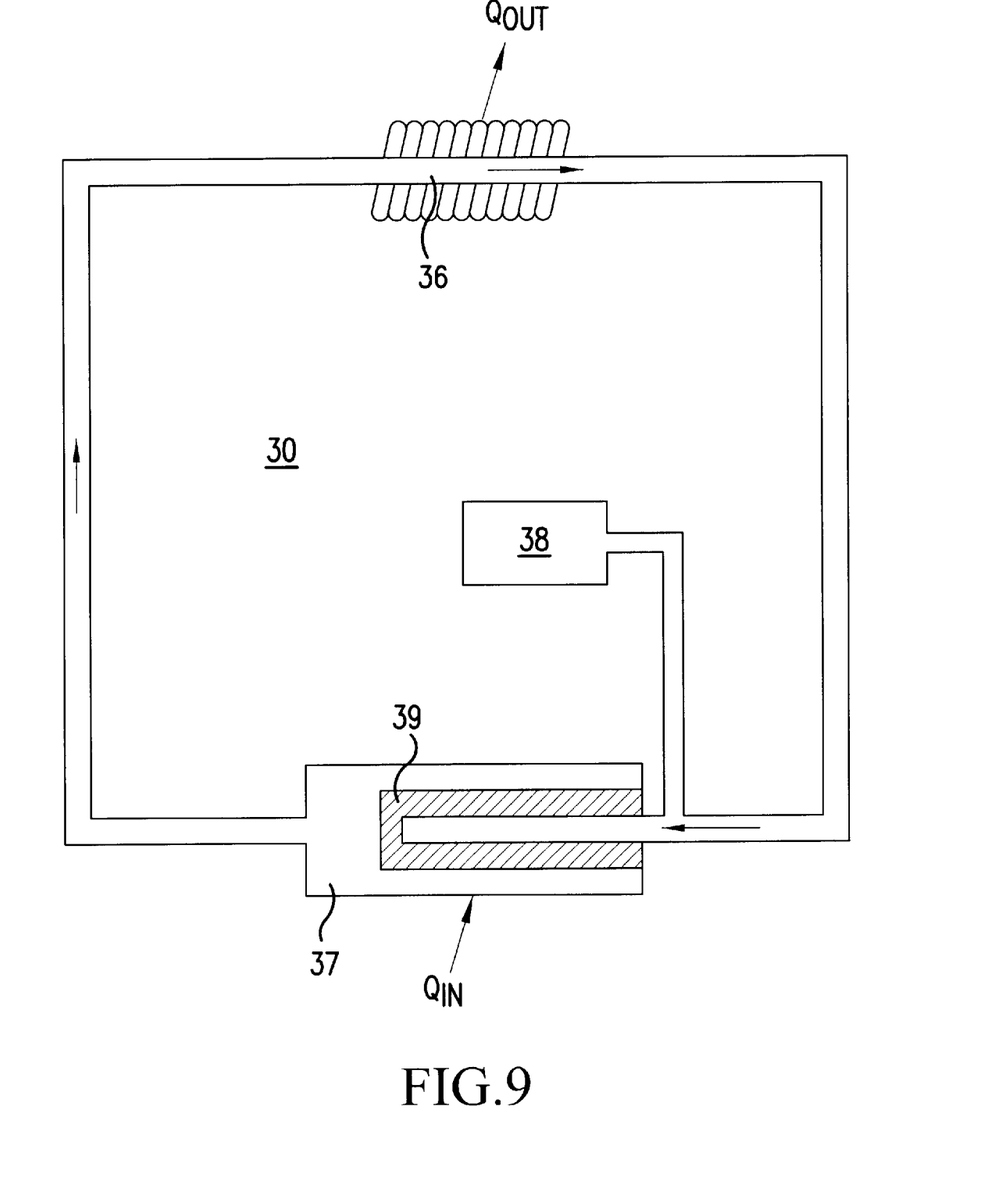
FIG. 9 is a schematic view of a loop heat pipe according to an embodiment of the present invention.

The present invention will now be described with reference to the accompanying drawings. FIG. 1 is a perspective view of a heat exchange device according to an embodiment of the present invention. FIG. 2 is a side view of a heat exchange device according to an embodiment of the present invention. FIG. 3 is an end view of a heat exchange device according to an embodiment of the present invention. FIG. 4 is a partial, exploded perspective view of an upper half of a heat exchange device according to an embodiment of the present invention. FIG. 5 is a perspective view of a disposable container according to an embodiment of the present invention. FIG. 6 is a side view of the disposable container shown in FIG. 5. FIG. 7 is an end view of the disposable container shown in FIG. 5. FIG. 8 is a side, cross-sectional, operational view of a heat pipe according to an embodiment of the present invention. FIG. 9 is a schematic view of a loop heat pipe according to an embodiment of the present invention.

While the present invention can be utilized in a wide range of direct tissue or blood temperature regulation applications, preferred embodiments of the present invention will described hereinafter with specific applicability to the temperature regulation of blood during cardiopulmonary procedures. However, one of skill in the art will appreciate that the present invention will vary greatly in size, shape and configuration, depending on the temperature regulation application to which the present invention is applied.

As seen in FIG. 1 through FIG. 4, a heat exchange device 10 is provided with a plurality of thermoelectric modules 40 that act as fully reversible heat pumps. Thermoelectric modules 40 move heat from one side of the module 40 to the other, dependant on the direction of the current supplied to the modules. Current is supplied to the thermoelectric modules via wire elements 45.

Blood enters the heat exchange device 10 through an inlet to a proportionally long, narrow disposable container 11. The blood is heated or cooled to the desired temperature and subsequently exits from an opposite end of the container 11.

As seen in FIG. 5 through FIG. 7, the disposable container 11 includes a pair of long, flat plates 1,2 facing each other in relatively close proximity. Plastic end pieces 3, 4 are provided at each end of the plates 1,2. The plastic end pieces 3,4 that transition the blood between transport tubing (not shown) and the plates 1,2. An ingress section 5 is provided between the plates 1, 2 to transition the fluid into a proportionally thin layer 15 that improves available fluid surface area for heat transfer. An egress section 6 transitions the blood back to standard/transport tubing (not shown).

This container 11 results in minimum blood side pressure drop and facilitates a gentle handling of blood. The blood is smoothly transitioned from transport tubing into a thin laminar flow layer and back to tubing, all within the interior of the disposable container 11.

The blood transport container 11 is placed in the heat exchange device 10 having the thermoelectric (TEC) modules 40 that contact a majority of surface area opposite the blood side of both flat plates, 1,2 of the container. As seen in FIG. 2, two heat sinks 20 with two attached Loop Heat Pipes (LHP) 30 may be provided to facilitate waste heat removal when operating the TEC modules 40 for maximum cooling.

Another embodiment of a disposable blood interface for the present invention includes a container 11 pressed into the same thermoelectric apparatus 10. As seen in FIG. 1, instead of a disposable container 11 having plates 1,2, the container 11 can be a length of flexible tubing. In both embodiments, the length of the flat plates or tubing, as well as the number of thermoelectric modules 40, will be determined by the temperature change requirements of the medical application.

A third embodiment includes very small TEC modules 40 attached directly to a small diameter Loop Heat Pipe (LHP) 30. This results in a heating and cooling catheter or probe for direct, waterless temperature regulation in the brain or other internal organs of the body. FIG. 8 and FIG. 9 show examples of various heat pipes 30 that are anticipated as applicable to the present invention. For example, a heat sink 20 having a plurality of fins 24 (as seen in FIG. 1 through FIG. 4) may serve as the heat sink in FIG. 8 and FIG. 9 designated by $Q_{OUT}$ (Heat Out of the system) on the condenser side 35 of the heat pipe 30. The evaporator side 36 of the heat pipe will typically require a heat source $Q_{IN}$ (Heat Into System), such as TEC modules 40.

Heat pipes 30 are provided with an enclosed heat pipe fluid in a vacuum or evacuated system. The fluid enclosed within the heat pipe 30 is heated in the evaporator side 36 of the heat pipe 30 in a preferred embodiment by heat from the TEC modules 40. As the fluid changes state into a vapor/liquid (mixed) and vapor phases, the vapor/liquid rises to the condenser side 35 of the heat pipe 30. The finned heat sink 20 serves as a means for extracting the additional energy from the vapor and subsequently facilitates condensation of the heat pipe fluid back into a liquid.

The condensed fluid returns to the evaporator side of the heat pipe 36 through a capillary, pumping action imparted by a porous wick 39. A reservoir 38 is preferably provided on the inlet side of the evaporator 36 in order to maintain preferred fluid levels across varying degrees of heat loading.

For cardiopulmonary applications, the thermoelectric devices 40 are arranged along the proportionally long fluid path so that feedback from sensors, 7,8,9 can be obtained. The sensors 7,8,9 independently control each thermoelectric module 40. The sensors 7,8,9 measure blood temperatures as the blood moves through the blood interface container 11. The exact temperatures of the blood are input into a computer control system (not shown). Based on output from the temperature sensors 7,8,9, a software program will automatically adjust voltage and current supplied to the thermoelectric modules 40 via the wire elements 20 to achieve a desired temperature change.

Two primary attributes of this system, individual control of the TEC modules 40 and the shape attributes of the blood/heat exchanger interface, combine to provide the maximum heating efficiency possible within the clinical prescribed 10° temperature differential for blood temperature change.

The improvements over the background art are due to the present invention's capability to maintain the clinically prescribed 10° temperature differential between the blood and the heating plates 1, 2 throughout the blood/heat exchanger interface. The attributes of this configuration results in a blood/heat exchanger interface or disposable container 11 that has the 21 sq. in of surface area needed to achieve maximum temperature change within clinical guidelines. The amount of saline typically used to "prime" blood-handling devices is 12 ml.

Since there is no clinically prescribed temperature differential limit for rapid, extreme cooling, the present invention permits the TEC modules 40 to operate at voltages and current that provide maximum energy transfer conditions and/or as is appropriate for the desired temperature change. In all cases, the TEC modules 40 are used with a uniquely designed, disposable heat exchange unit in order to reach desired temperatures with the least number of thermoelectric modules 40 and amount of blood contact on foreign surfaces.

The operation of TEC modules 40 for maximum cooling, as indicated for direct blood or bodily tissue applications, requires an effective way to remove waste heat. Clinical advantages of the present invention for the identified medical applications are dependent on its highly efficient cooling. Consequently, during cooling, TEC modules 40 must be run at peak conditions.

Approximately 270 W of waste heat must be removed from the hot side of an 80 W TEC module to maintain the TEC module 40 at peak conditions. It is improbable that this amount of heat can be removed by convection with a system that would fit within the space and noise constraints of identified medical applications, particularly passive operation of the heat exchange device 10 through implantation within a patient.

In order to keep within typical hospital Operating Room (OR) space and noise constraints, some type of fluid flow is indicated when running 80W TEC modules at maximum energy transfer conditions. Unfortunately, the use of a fluid increases the complexity of the device, compromises user convenience and reduces other advantages of TECH devices.

In order to remove waste heat, a preferred embodiment uses Loop Heat Pipe (LHP) Technology in conjunction with a heat sink 20 to remove waste heat. LHP's are similar to the more conventional heat pipes 30 shown in FIG. 8. Each Heat pipe 30 uses passive, capillary pumping and two-phase heat transfer. Each heat pipe 30 can transfer heat efficiently with relatively small temperature differentials. Each heat pipe 30 operates passively, with no external power requirements, moving parts, vibration or maintenance. Accordingly, the present invention may incorporate either type of heat pipe 30 within the heat exchange device 10.

However, LHP's avoid many of the limitations of conventional heat pipes. The liquid and vapor flow in series in an LHP, not against each other as seen in the more conventional heat pipe 30 of FIG. 8. The wick 39 is confined to the evaporator side 36 of the LHP 30, rather than running the entire length of the device. Accordingly, the LHP avoids the liquid flow losses in the wick often experienced in a conventional heat pipe 30 (FIG. 8). Since the LHP's can utilize a relatively small length of wick 39, very small pore-size wicks 39 can be used in identified medical applications that still satisfy high thermal transport requirements.

Small pore-size wicks 39 provide the capability to have tubular, extremely small heat exchange devices 10 as compared to the larger, rectangular heat exchange device 10 likely to be used in cardiopulmonary applications. Therefore, it is possible to manufacture a small diameter, direct contact, waterless, heating and cooling catheter or probe for internal use in the brain or other parts of the body with maximum thermoelectric cooling effect.

Since there is no wick 39 in the liquid or vapor lines, the lines of the heat pipe 30 can be made of standard flexible tubing. This is a significant advantage in all possible applications, as it provides user convenience and keeps the heat exchange device compact, inexpensive and easily moved. As a result, the present invention permits placement of a heat exchange device 10 in close proximity to the patient and blood transport tubing will be much shorter than conventional systems.

A LHP 30 is included in the heat exchange device 10 of a preferred embodiment. The design and performance features of LHPs provide adequate heat exchange in a cardiopulmonary system and make possible extremely small tubular heat exchange systems. LHP's simple design and passive heat transport system with no moving parts, practically eliminates maintenance and operator attention. Easy, reliable startups (the operator starts the device 10 by simply applying heat to the evaporator 36) require no user interaction. Routable, flexible, small-diameter transport lines aid the packaging of the heat exchange device 10 and facilitate a space-conserving, inexpensive alternative to the background art.

One of the major benefits of the present invention is convenient, reliable capability to change system temperature settings quickly. Adherence to the surgeon's protocol must be straightforward and reliable. LHP's 30 provide a key element of a preferred embodiment of the present invention's blood temperature regulation system as they can operate as a constant or variable conductive device, with seamless transition between modes.

The components of the present invention can be fabricated by a number of well recognized processes and may utilize a variety of raw materials. A particular concern involves compliance with the standards, review and approval procedures of the FDA (Food and Drug Administration). It will be appreciated that materials for the present invention, particularly those to be implanted within the patient, will require materials that are compatible with a patient's body.

Stainless steel plate and/or sheet can be utilized for the heat sink 20 and/or container 11. Alternatively, molded plastic can also be utilized for the present invention, including plastic tubing. Further, the heat exchange device 10 can be constructed from a variety of commercial, off the shelf equipment such as temperature sensors, thermoelectric modules (e.g., 80 W modules), programmable power supply modules, Thermosython, fans, LED displays and associated computer hardware and software.

As aforementioned, many of the related systems of the background art rely upon water as a cooling/heating medium. Further, existing blood interface devices have complex blood paths that complicate setup and use. These devices add a significant amount of surface area and prime volume to the CPB circuit. The present invention does not use water, reduces surface area (necessary tubing and blood/heat exchanger interface) and thereby reduces necessary priming with saline solutions by as much as 80%.

In a preferred embodiment, thermoelectric modules 40 are automatically operated at a maximum level needed to maintain the 10 degree temperature limitation (clinically recommended) between the blood and heating medium throughout the blood interface disposable. The operator sets a temperature and a control system maintains maximum energy transfer conditions in thermoelectric modules on the heat exchanger to achieve desired temperatures.

It is further anticipated that numerous safety features that correct potentially dangerous situations and alert the operator may be incorporated into the present invention. The convenience of automatic control also increases the safety of the device as maximum temperature regulation can be achieved with the least amount of operator intervention. This will free up medical personnel such as perfusionists and other professionals from different concerns.

An alternative embodiment of the present invention includes a long, small diameter Loop Heat Pipe (LHP) 30 heat exchanger having thermoelectric modules 40 and sensors 7,8,9 directly mounted thereon. Since the shape of the blood contact container 11 and heat exchange device 10 allows the thermoelectric modules 40 to be arranged for maximum blood interface contact and control, the heat exchanger 10 could be operated internal to the body in this embodiment.

The fact that the shape of the blood interface is a proportional, long rectangle facilitates its capability to efficiently change blood temperature. The unique blood contact disposable, individual control of thermoelectric modules 40 and automatic regulation allows thermoelectric modules 40 to be operated at maximum efficiency within clinical guidelines.

As aforementioned, a minimum quantity of priming solution is needed for extracorporeal applications with the present invention. A Cardio Pulmonary Bypass (CPB) circuit is typically primed with a saline solution prior to introducing blood. The clinical benefits of reducing prime solution and blood contact with foreign surfaces are well documented. The present invention uses the same amount or less priming saline than would be required in standard medical grade PVC blood transport tube of the same length. For extracorporeal blood flow, the blood contact container 11 is placed in a thermoelectric heat exchanger 10. However, for internal blood flow, the Thermoelectric LHP can be placed directly into the blood flow.

The TEC modules 40 can be individually operated at conditions so that the blood temperature is changed to the desired temperature on a single pass through the disposable, blood interface container 11 when the ideal number of TEC modules 40 is selected for each application. This method is ideally suited to meet the inherent complexity of delivering adequate temperature regulation performance combined with adherence to the clinical guidelines for patient safety required for cardiopulmonary surgery, neurovascular procedures or other medical applications.

Due to the nature of thermoelectric modules with their resistive "waste" heat effect, an effective heat removal is required in order to permit operation of the thermoelectric modules at peak performance for cooling. The present invention proposed loop heat pipes (LHPs) to remove waste heat. The use of LHP's allow compact heat exchangers which allows the heat exchangers to be placed in close proximity to the patient. The small size and flexible tubing of LHPs makes the handling of heat exchangers additionally convenient.

The present invention allows the temperature of blood to be more quickly adjusted than with the use of water as the energy medium. The almost instantaneous response time of thermoelectric modules 40 provides the capability to immediately respond to changes in energy transfer conditions at the heat exchanger. This capability allows the practitioner to quickly and effectively change blood temperatures and to more accurately follow the temperature regulation protocol established by the surgeon.

The present invention offers the added advantage of simplicity at the blood interface. The relatively simple, disposable container 11 places less shear force on the blood. The disposable blood container 11 has ingress (inlet) and egress (outlet) sections to gently transition the blood from transport tubing to the heat transfer region and back again to tubing. If transparent tubing is desired, the heat exchange region also has good visibility at the perimeter of the heat exchange plates 1,2 to allow the practitioner to view the blood or fluid as it travels through the heat exchange device 10.

The sensors 7,8,9, measure blood temperatures as the blood moves through the blood interface container 11 and the exact temperatures of the blood are input into a computer control system (not shown). A software program, resident in the control system, automatically adjusts voltage and current supplied to the thermoelectric modules to achieve desired temperature change. Heating and cooling operations can be controlled by controlling the direction of current through the desired thermoelectric devices 40.

The system of the present invention can be easily configured for specific medical applications. Heat exchangers can be sized for particular applications. The minimum surface area and priming volume can be obtained for a desired temperature change. Accordingly, various sized units are possible with minimal impact on overall heat exchange performance.

U.S. Pat. No. 4,476,685 to Aid and U.S. Pat. No. 4,309,592 to LeBoeuf, although directed toward distinct heat exchange method and apparatus from that of the present invention, generally describe many of the manufacturing, materials and assembling processes that are commonly utilized in the related art. The details of these materials, apparatus, and manufacturing processes are herein incorporated by reference to the present invention.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A heat exchange device for heating and cooling of a physiological fluid, said device comprising:

a pair of modules arranged in a spaced apart relationship, wherein said modules include a plurality of individually controlled thermoelectric devices;

a container providing a flow path for said fluid, said container interposed between said thermoelectric devices;

at least one heat sink for dissipating heat from said device;

at least one sensor arranged within the container and providing a temperature of said fluid along said flow path; and at least one heat pipe; and a plurality of wire elements connectable with said thermoelectric devices, wherein each heat pipe is a loop heat pipe.

2. The heat exchange device according to claim 1, each heat pipe effectuating heat transfer from said thermoelectric devices to each heat sink.

3. The heat exchange device according to claim 1, each sensor providing a temperature signal for individually controlling said thermoelectric devices.

4. The heat exchange device according to claim 1, further comprising a plurality of additional thermoelectric devices arranged along a length of said flow path, said container disposed between said additional thermoelectric devices.

5. The heat exchange device according to claim 1, said heat sink including a plurality of fins for accelerating heat transfer.

6. The heat exchange device according to claim 1, wherein said container includes plastic tubing.

7. The heat exchange device according to claim 1, wherein said container includes a pair of long, narrow plates forming the flow path therebetween, an inlet, an outlet, and a pair of end pieces.

8. The heat exchange device according to claim 4, wherein said container includes a pair of long, narrow plates forming the flow path therebetween, an inlet, an outlet, and a pair of end pieces.

9. A system for controlling a fluid temperature of a physiological fluid, said system comprising:

a control system for setting and controlling the fluid temperature;

a software program resident in the control system;

a disposable container providing a flow path for said fluid;

a plurality of thermoelectric devices arranged along and across said flow path of the container, wherein said container is interposed between said thermoelectric devices, said thermoelectric devices imparting individualized temperature control of said fluid temperature;

a plurality of sensors arranged within the container and providing a temperature signal of said fluid to said control system;

at least one heat pipe;

at least one heat sink for dissipating heat from said system;

an oxygenator; and a plurality of transport tubing connecting said container to said oxygenator.

10. The system according to claim 9, wherein said control system varies a voltage and a current to each thermoelectric device in response to said temperature signal from each sensor through a plurality of wire elements connectable with said thermoelectric devices.

11. The system according to claim 9, each heat pipe effectuating heat transfer from said thermoelectric devices to each heat sink.

12. The heat exchange device according to claim 9, wherein each heat pipe is a loop heat pipe.

13. The heat exchange device according to claim 9, each heat sink including a plurality of fins for accelerating heat transfer.

14. The heat exchange device according to claim 1, wherein said container includes plastic tubing.

15. The heat exchange device according to claim 9, wherein said container includes a pair of long, narrow plates forming the flow path therebetween, an inlet, an outlet, and a pair of end pieces.

16. A method for controlling a fluid temperature of a physiological fluid, said method comprising the steps of:

providing a disposable container having a flow path for said physiological fluid between a plurality of thermoelectric devices operatively connected to a control system;

setting the fluid temperature of the fluid to a target temperature through the control system;

adjusting the fluid temperature with the thermoelectric devices to obtain the target temperature based upon temperature output signals received from a plurality of sensors arranged along and across the flow path; and providing a heat sink for dissipating heat from said thermoelectric devices and at least one heat pipe for transferring energy between said container to said heat sink.

17. The method according to claim 16, wherein the physiological fluid is blood.

18. The method according to claim 16, wherein said container is configured to be utilized as either a stand alone heat exchanger or integrated with an oxygenator.

19. The method according to claim 16, wherein a maximum temperature differential between a temperature of the fluid and a heat source temperature is 10 degrees Fahrenheit.

* * * * *